United States Patent [19]

Brüggemann et al.

[11] Patent Number: 5,721,295
[45] Date of Patent: Feb. 24, 1998

[54] POLYMER COMPOSITION, ABSORBENT COMPOSITION, THEIR PRODUCTION AND USE

[75] Inventors: Helmut Brüggemann, Duisburg; Uwe Günther, Tönisvorst; Helmut Klimmek, Krefeld, all of Germany

[73] Assignee: Chemische Fabrik Stockhausen GmbH, Krefeld, Germany

[21] Appl. No.: 535,069

[22] PCT Filed: May 3, 1993

[86] PCT No.: PCT/EP93/01060

§ 371 Date: Jan. 26, 1996

§ 102(e) Date: Jan. 26, 1996

[87] PCT Pub. No.: WO94/25519

PCT Pub. Date: Nov. 10, 1994

[51] Int. Cl.$^6$ .................. C08L 1/28; C08L 3/08; C08L 5/07
[52] U.S. Cl. .................. 524/44; 524/45; 524/50; 524/55
[58] Field of Search .................. 502/404; 134/40, 134/41, 42; 210/660, 767; 252/194, 315.3; 604/368; 524/28, 42, 43, 44, 45, 47, 50, 55

[56] References Cited

U.S. PATENT DOCUMENTS

| | | | |
|---|---|---|---|
| 4,373,036 | 2/1983 | Chang et al. | 524/43 |
| 4,587,284 | 5/1986 | Lüssi et al. | 524/28 |
| 4,693,713 | 9/1987 | Chmelir et al. | 604/368 |
| 4,755,544 | 7/1988 | Makino et al. | 524/43 |
| 4,952,550 | 8/1990 | Wallach et al. | 502/404 |
| 4,959,341 | 9/1990 | Wallach | 502/404 |
| 4,997,867 | 3/1991 | Federström et al. | 524/47 |
| 5,073,202 | 12/1991 | Wallach | 210/660 |
| 5,264,471 | 11/1993 | Chmelir et al. | 524/43 |
| 5,417,679 | 5/1995 | Toms et al. | 524/47 |

Primary Examiner—Peter A. Szekely
Attorney, Agent, or Firm—Foley & Lardner

[57] ABSTRACT

A polymer composition, in particular an absorbent composition or an active substance-containing depot material are disclosed which substantially consist of a water-soluble and/or water-swellable polymer based on polysaccharides as the main component, and of a water-swellable polymer as further component, used as polymeric components, and of a matrix material for the prevention of separation and gel blocking, an ionic or covalent cross-linking agent, a reactive additive, as well as of an anti-blocking agent. Additionally, their production and use as well as (animal) hygiene items and chemico-technical products are disclosed which comprise these polymer compositions or absorbent compositions.

34 Claims, No Drawings

POLYMER COMPOSITION, ABSORBENT COMPOSITION, THEIR PRODUCTION AND USE

The present invention relates to a polymer composition and an absorbent composition (absorbing materials) which are mainly based on renewable raw materials. For this reason they are biodegradable in principle. Owing to the mainly native origin, the absorbents do not comprise residual monomers, or considerably lower amounts thereof, as compared with absorbers based on polyacrylate. The absorbers according to the present invention have a comparatively high absorption capacity and absorption rate, also under load, for water and aqueous solutions, no tendency to gel blocking (gel blocking: on contact with water the outer layers of the absorber stick together and prevent further advancement of the liquid into the absorber), and they are mechanically stable (with respect to the separation into the individual components). In swollen condition they separate into individual particles; they are non-aqueous and have a very high gel stability. The present invention further relates to a process for their production and to their use as fiber, film, powder, or granular material for the absorption of water, aqueous solutions or aqueous dispersions and body fluids in hygiene articles, such as tampons or diapers, in animal hygiene articles, in technochemical products, for example, packaging materials, in particular for meat and fish, in culture pots, as well as in soil conditioning and as cable sheathings.

Most of the absorbing materials used today, also referred to as superabsorbers, which are capable of absorbing large amounts of liquid (water, urine) within a short period of time, primarily are slightly cross-linked polyacrylates; therefore they are not based on renewable raw materials and their biodegradability is comparatively insufficient or they are not biodegradable at all.

Endeavoring to build up superabsorbers of renewable raw materials, acrylic acid was grafted on polysaccharides, for example on corn starch, as is described in DE-C-2612846. However, only small amounts of polysaccharides (up to a maximum of 25%) may be used, otherwise the absorption properties will deteriorate dramatically.

By incorporating polysaccharides into the polymerization gel of polyacrylates, as is described in DE-OS 40 29 591, 40 29 592, and 40 29 593, the polyacrylates can also only be replaced to the extent of a maximum of 25%, without resulting in a clear deterioration of the absorption capacity and other properties of the resulting superabsorbers, even if various auxiliary agents are added additionally, such as fibers and, for example, aluminum cross-linkers. The polysaccharides are considered to be fundamental elements for the absorbers to obtain biodegradable units.

DE-C-3132976 describes the mixing of polyacrylic acid with polysaccharides in powdery form and in solution, wherein the shell of the absorber particles of the mixtures are cross-linked with aluminum cross-linking agents, such as $Al(OH)_2OOCCH_3 * \frac{1}{3} H_3BO_3$. Thus, this process cannot provide superabsorbers consisting by more than 60% of renewable raw materials.

According to the processes described in the art, the polysaccharides do not contribute much as an absorption component.

Various patent publications, such as DE-A-2634539, describe the production of carboxymethylcellulose-absorbers, i.e., of materials which are biodegradable in principle, by cross-linking the carboxymethylcellulose with various cross-linking agents in aqueous system. However, these absorbers show severe gel blocking.

U.S. Pat. No. 4,959,341 describes the production of an absorber based on carboxymethylcellulose, which consists of a mixture of carboxymethylcellulose, cellulose fibers, a hydrophobic component, and $Al(OH)_2OOCCH_3 * \frac{1}{3} H_3BO_3$ as cross-linking agent, with the aluminum cross-linking agent causing a cross-linkage of the carboxymethylcellulose during the liquid absorption.

These absorbers have good absorption properties, however, show blocking phenomena. Additionally, these absorbers can easily be separated by mechanical stresses, such as sieving or conveying, so that they are no longer present as a homogeneous product, this restricts their applicability to a great extent.

EP-B 0 201 895 also describes the production of an absorber based on carboxymethylcellulose. However, in the production of these absorbers an aqueous solution is used in which the carboxymethylcellulose is present in a low concentration. Additionally, larger amounts of organic solvents are required in the production. The production of these carboxymethylcellulose-absorbers is very time-consuming. The absorbers themselves show blocking phenomena and have a low gel strength.

Initially, only the very high swelling capacity on contact of the absorber with the liquid, also referred to as free swelling capacity, had been the main factor in the development of superabsorbers; later it turned out, however, that not only the amount of absorbed liquid but also the gel strength is of importance. However, absorbency, also referred to as swellability or free swelling capacity, on the one hand, and gel strength of the cross-linked polymer on the other hand, represented contrary properties, as is known by U.S. Pat. No. 3,247,171 (DOW/WALKER) and U.S. Pat. No. Re 32,649. This means that polymers having a particularly high absorbency exhibit a poor strength of the swollen gel so that the gel is deformable under an exerted pressure (e.g., load of a body) and further liquid distribution and liquid absorption is prevented. According to U.S. Pat. No. Re 32,649 a balanced relation between absorption capacity (gel volume) and gel strength should be aimed at so as to ensure liquid absorption, liquid transport, dryness of the diaper and the skin, when these superabsorbers are used in a diaper construction. In this connection, not only is the polymer's capability of retaining a liquid under subsequent pressure, after swelling freely first, of importance, but also the fact that liquids are absorbed even against a simultaneously acting pressure, i.e., during the liquid absorption. This is the case in practice when a baby or person sits or lies on a sanitary article, or when shear forces are acting, e.g., by movements of legs. In EP-A-0 339 461, this specific absorption property is referred to as absorption under load ("AUL").

It was the object of the present invention to provide a polymer composition and an absorbent composition (in the following referred to as absorber) in a simple manner, which does not have the drawbacks described above and which has the following properties:

a) The absorber shall mainly consist of components of a native origin and thus be biodegradable in principle.

b) The absorbers shall have a high mechanical strength, they must not separate into their individual components during sieving or, for example, in a helical screw feeder.

c) The absorbers shall have a comparatively high absorption rate and absorption capacity, also under load, for water and aqueous solutions.

d) The content of residual monomers shall be considerably lower than in conventional absorbers based on polyacrylates.

e) The absorbers shall have a very high gel stability in swollen condition; in this connection the absorber particles shall be present in the form of separated, individual particles.

f) They must not show a tendency to gel blocking.

g) The absorbers shall have a high absorption rate and absorption capacity under load for water and aqueous solutions.

h) The absorbers shall be comparatively easy to manufacture.

According to the present invention this object is achieved by an absorber substantially consisting of five components:

a component A based on special reproductive polysaccharide raw materials, a component B consisting of special water-swellable polymers, a matrix material, an ionic or covalent cross-linking agent, a reactive additive, as well as optionally, of an added anti-blocking agent.

Thus, the present invention relates to a polymer composition substantially consisting of 70–99.99%-wt. of a component A based on water-soluble and/or water-swellable polymers based on polysaccharides and their derivatives which have optionally been modified by ionic and/or covalent cross-linkage, and 0.01–30%-wt. of a component B based on water-swellable, synthetic polymers and/or copolymers based on (meth-) acrylic acid, (meth-) acrylonitrile, (meth-) acrylamide, vinyl acetate, vinyl pyrrolidone, vinyl pyridine, maleic acid (-anhydride), itaconic acid (-anhydride), fumaric acid, vinyl sulfonic acid and/or 2-acrylamido-2-methylpropane sulfonic acid, as well as the amides, N-alkyl derivatives and N,N'-dialkyl derivatives, the hydroxyl group-containing esters and amino group-containing esters of these polymerizable acids, with 0–98% of the acid groups being neutralized, and these polymers and/or copolymers being cross-linked of at least one compound which is at least bifunctional, 0.1–30%-wt., relative to the polymer components A and B, of a matrix material having a melting or softening point of below 180° C. for the prevention of separation and gel blocking, 0.001–10%-wt., relative to the polymer components A and B, of an ionic and/or covalent cross-linking agent, 0.1–50%-wt., relative to the polymer components A and B, of a reactive additive for the improvement of the absorption capacity and/or absorption rate, and 0–50%-wt., relative to the polymer components A and B, of an anti-blocking agent based on natural or synthetic fibers or on large-surface materials.

Additionally, the present invention relates to an absorbent composition having the above composition, and to an active substance-containing depot material composition having the above composition and releasing the active substance in a sustained manner.

Most surprisingly, it was found that a slight addition of component B to component A causes a distinct improvement in the absorption properties. Since only slight additions of component B are required, the residual monomer content, e.g., of acrylic acid, of such an absorber is clearly lower than that of absorbers based on polyacrylates.

Furthermore, it was surprisingly found that by the addition of a solid matter, which serves as a matrix for the absorber system, in combination with the polymeric absorbent, a mixture of the components A and B, and an ionic cross-linking agent, a reactive additive and optionally an anti-blocking agent, an absorbent can be produced which has a high absorption rate and absorption capacity for water and aqueous solutions as well as an improved mechanical strength with respect to separation of the individual dry particles. Additionally, the gels of this absorber system are present separately in individual particles.

Most surprisingly, the reactive additive improves the absorption properties, in particular also under load.

Most surprisingly, these absorbers—in combination with the above-mentioned properties—additionally have a gel strength that is considerably higher than that of absorbers built up on a polyacrylic acid basis.

Water-soluble and water-swellable polymers based on polysaccharides and their derivatives are suitable as component A, such as guar, carboxymethyl guar, xanthan, alginates, gum arabic, hydroxyethylcellulose or hydroxypropylcellulose, carboxymethylcellulose and other cellulose derivatives, starch and starch derivatives, such as carboxymethyl starch and mixtures of the individual polysaccharides. The preferred polymers are the anionic derivatives of starch, guar, and cellulose, with carboxymethylcellulose representing a particularly preferred material.

The listed polymers of component A may be modified by a cross-linkage in order to reduce their solubility in water and to achieve better swelling properties. The cross-linking may take place both in the whole polymer or only on the surface of the individual polymer particles.

The reaction of the polymers may be effected with ionic cross-linkers, for example, calcium, aluminum, zircon, and iron(III) compounds. The reaction may also be effected with polyfunctional carboxylic acids, such as citric acid, mucic acid, tartaric acid, malic acid, malonic acid, succinic acid, glutaric acid, adipic acid, with alcohols, such as polyethylene glycols, glycerol, pentaerythritol, propanediols, saccharose, with carbonic acid esters, such as ethylene and propylene carbonate, with amines, such as polyoxypropylene amines, with epoxy compounds, such as ethylene glycol diglycidyl ether, glycol diglycidyl ether or glycol triglycidyl ether and epichlorohydrin, with acid anhydrides, such as succinic anhydride and maleic anhydride, with aldehydes and polyfunctional (activated) olefins, such as bis-(acrylamido)-acetic acid and methylene bisacrylamide.

Of course, derivatives of the mentioned compound classes as well as heterofunctional compounds with different functional groups of the above-mentioned compound classes are also suitable.

Suitable as component B are water-swellable synthetic polymers or copolymers primarily based on (meth-) acrylic acid and also based on (meth-) acrylonitrile, (meth-) acrylamide, vinyl acetate, vinyl pyrrolidone, vinyl pyridine, maleic acid, maleic anhydride, itaconic acid, itaconic acid anhydride, fumaric acid, vinyl sulfonic acid, 2-acrylamido-2-methylpropane sulfonic acid, as well as the amides, their N-alkyl derivatives and N,N'-dialkyl derivatives, hydroxyl group-containing esters and amino group-containing esters of the polymerizable acids. Cross-linked, partially neutralized polyacrylates are preferred.

Up to 98%, preferably 50–80%, of the acid groups may be neutralized.

The polymers may be cross-linked by an at least bifunctional cross-linking agent.

The production of these above-mentioned polymers is effected according to known processes (DE-C-27 06 135, DE-OS 40 15 085). Polyacrylates, e.g., the FAVOR®-types manufactured by Chemische Fabrik Stockhausen GmbH, represent a particularly preferred material as component B.

Organic solid substances melting or softening below 180° C. and preferably having a soft consistency at room temperature are suitable as matrix, for example, triglycerol monostearate or wax esters. Highly viscous liquids, such as castor oil are also suitable.

For preference, polycaprolactones are suitable as the matrix, such as TONE 0230 and 0240 from Union Carbide, which may also be modified, e.g., by a reaction with maleic anhydride.

The matrix imparts a higher mechanical strength to the absorber system, presumably by chemical and/or physical interactions; this considerably reduces separation of the individual components during transports, e.g., by means of a conveyor screw or by screening. Thereby an absorbent can be manufactured which has high absorption values and, moreover, is present as a more homogeneous and thus more effective system, after finishing or incorporation into its intended place.

Additionally, embedding the absorption agent in the matrix most surprisingly results in a clear reduction or even complete elimination of gel blocking, thus ensuring a high absorption rate throughout the absorber. Furthermore, the matrix firmly fixes the cross-linking agent at the surface of the individual absorber particles.

The granulation of superabsorber fine dusts by means of agglomeration auxiliary agents is described in the examples of DE-PS 37 41 157 and DE-PS 39 17 646. The products thus produced have a high absorption rate for water and aqueous solutions. However, these products completely consist of polyacrylates and for this reason they are poorly—if at all—biodegradable. The agglomeration agents merely have a function in the granulation of a product, but not as a matrix material.

The anti-blocking agents also reduce gel blocking; thus they cause an accelerated and improved liquid absorption and ensure that the gels are separated, i.e., are present as individual particles.

As is generally known, suitable anti-blocking agents include fibrous materials and other large-surface materials (cf DE-C-31 41 098 and DE-C-33 13 344).

The fibers may be natural or synthetic ones, e.g., wool, cotton, silk and cellulose fibers, or polyamide, polyester, polyacrylonitrile, polyurethane fibers, fibers of olefins and their substitution products, as well as polyvinyl alcohol fibers and their derivatives. Examples of inorganic materials include, bentonites, zeolites, aerosils, and activated carbons.

Reactive additives result in an improvement in the absorption capacity and rate, in particular under pressure. Suitable reactive additives are substances increasing the concentration of the hydrophilic groups in the absorber and/or causing a modification of the absorber and/or increasing the flowability of the gel and/or reducing the electrolyte concentration in the liquid to be absorbed. The reactive additive may be combined with the other components, either chemically or physically. Suitable reactive additives include surfactants, ion-exchangers—in particular cation exchangers—or metallic salts or complexes which are capable of hydrolyzing during preparation of the absorber system; in this connection, the reactive additive may completely or partially replace the anti-blocking agent.

A particularly preferred material for the reactive additives is titanyl sulfate.

Suitable cross-linking agents are compounds converting the above-mentioned polymers into a state in which the water-solubility is reduced, the suction power improved, and the block phenomena diminished.

Metallic compounds which can interact with the functional groups of the polymers are suitable ionic cross-linking agents, Particularly preferred are magnesium, calcium, aluminum, zircon, iron, and zinc compounds which have an excellent solubility in water, such as the salts of carboxylic acids and inorganic acids.

Preferred carboxylic acids are acetic acid, lactic acid, salicylic acid, propionic acid, benzoic acid, fatty acids, malonic acid, succinic acid, glutaric acid, adipic acid, citric acid, tartaric acid, malic acid, and mucic acid.

Preferred inorganic anions include chlorides, bromides, hydrogen-sulfates, sulfates, phosphates, borates, nitrates, hydrogencarbonates, and carbonates.

Additionally suitable are organic compounds comprising multivalent metals, such as actylacetonates and alcoholates, e.g., iron and zirconium acetylacetonates such as Fe(acac)$_3$ and Zr(acac)$_4$, and titanium and zirconium alcoholates of butanol and propanol such as Ti(OBu)$_4$ and Zr(o-prop)$_4$.

The water-soluble cross-linking agent causes a crosslinkage of the components A and B, both with each other and between each other, in particular at the surface, thus improving the absorption properties, as is described in DE-PS 31 32 976, DE-OS 26 09 144, and U.S. Pat. No. 4,959,341.

Suitable covalent cross-linking agents are polyfunctional carboxylic acids, alcohols, amines, epoxy compounds, carboxylic acid anhydrides, and aldehydes as well as their derivatives. Examples thereof include citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate, and propylene carbonate.

Also suitable are natural derivatives of the listed compounds as well as heterofunctional compounds with different functional groups of the above-mentioned compound classes.

The proportion of component A in the ratio of component A to component B amounts to 70–99.99%-wt., preferably 75–90%-wt. The portion of component B amounts to 0.01–30%-wt., preferably 10–25%-wt.

The addition of component B—even in small amounts—causes a considerable improvement in the absorption properties, in particular with respect to the suction power. As compared to a pure carboxymethyl cellulose (C.M.C.) material a surprisingly clear improvement in the absorption properties can thereby be achieved.

The amount of anti-blocking agent amounts to between 0.5 and 50%-wt., preferably 5–15%-wt., relative to components A and B.

The amount of reactive additive amounts to between 0.1 and 50%-wt., preferably 2–10%-wt., relative to the components A and B.

The amount of cross-linking agent in the absorber amounts to 0.001–10%-wt., preferably 3–7%-wt., relative to components A and B.

The addition of matrix material, relative to components A and B, shall amount to between 0.1–30%-wt., preferably between 2.5 and 7.5%-wt.

The matrix prevents the absorbent from disintegrating, as is observed in pure physical mixtures, e.g., in U.S. Pat. No. 4,952,550, and it additionally prevents gel blocking.

The preferred production of the absorbent is described in the following.

To manufacture the absorbent according to the present invention, component A and component B are physically mixed in dry condition at room temperature. This material is mixed with the anti-blocking agent, the reactive additive, and the matrix component until a homogeneous mixture results. Mixing of the components is effected in suitable mixers, such as screw mixers, fluidized bed mixers, disk mixers, or ribbon mixers.

The heat treatment is effected at 25°–180° C., preferably at 100°–120° C. The heating time amounts to 5–60 minutes, preferably 20–40 minutes. Conventional dryers or heating furnaces or ovens (e.g., disk dryers, conveyor dryers, fluidized bed dryers, or infra-red dryers) are used for the heat treatment of the product. Subsequently, the ionic cross-linking agent, preferably aluminum dihydroxyacetate stabilized with boric acid, is incorporated at room temperature until a homogeneous mixture results. For fixation purposes of the cross-linking agent by the matrix, heating to 25°–180° C., preferably to 50°–80° C., for 5–60 minutes is effected again, in order to melt the matrix material.

Components A and B may be screened prior to mixing, preferably in the range of 90–630 μm.

The incorporation of the matrix components is preferably effected at room temperature, however, the matrix component may also be used as a melt.

Prior to the thermal modification, an admixture preferably consisting of water/isopropanol may be added to the mixture, in order to have a solubilizer causing a thermal modification of component A, i.e., of a polysaccharide and not of polyacrylic acid, with each other, as well as with the matrix component and component B in the edge regions of component A; this has a positive effect on the suction power of the absorbent. Water and other admixtures of water with water-soluble organic solvents may also be used instead of the water/isopropanol-mixture.

EP-PS 0 083 022 describes the cross-linkage of an absorber, which consists of polyacrylic acid, with cross-linking agents comprising at least two functional groups and being able to react with the carboxyl groups of the polyacrylate. The reaction takes place at the surface of the absorber particles. DE-PS 33 14 019 and DE-PS 35 23 617 also describe the surface cross-linkage of polyacrylates by means of cross-linking agents having at least two functional groups. In contrast to the absorbers according to the present invention, these patents only describe modifications of polyacrylates—but not of polysaccharides—in the shell, however, this does by no means result in absorbers having a sufficient biodegradability.

The incorporation of the ionic cross-linking agent may also be effected directly into the physical mixture of component A, component B, anti-blocking agent, reactive additive, and matrix material, whereupon heating to 25°–180° C., preferably to 100°–120° C. is effected for 5–120 minutes, ideally 20–60 minutes.

In this process, the above-mentioned solvent-step may be effected either prior to or after the incorporation of the cross-linking agent.

The covalent cross-linking agent may be added to the polymer mixture as an alternative and in addition to the ionic cross-linking agent, either prior to or after the matrix addition.

The covalent cross-linking agent is dissolved in a preferably optional alcohol/water-mixture and dropped into the polymer mixture under rapid stirring. The quantity of solvent amounts to between 1 and 10%, relative to the polymeric mixture. Subsequently, heating to 25°–180° C. is effected for 5–120 minutes. Water and mixtures of water with water-soluble, organic solvents may be used as solvents.

The absorbent material according to the present invention has a good biodegradability, as compared to products based on polyacrylic acid, with a considerably improved absorption and suction capacity for a 0.9% solution of sodium chloride, also under load, as compared to known absorbents on a native basis, and a surprisingly very high gel strength.

Gel strength of some absorbers according to the present invention and some commercially known absorbers

| Product name | Gel strength (10 Hz) (N/m$^2$) |
| --- | --- |
| Absorbers according to the invention | |
| superabsorber of Example 4 | ≧10000 |
| superabsorber of Example 8 | =10000 |
| Commercially known Absorbers | |
| Product A | 2450 |
| Product B | 4200 |
| Product C | 3500 |
| Product D | 2700 |
| Product E | 4950 |
| Product F | 3700 |
| Product G | 1575 |

Products A, B, C, D, F, G:
cross-linked, partially neutralized polyacrylates
Product E:
cross-linked, partially neutralized polyacrylate-starch-graft polymer.

Additionally, the mechanical strength (with respect to disintegration into the individual components) is considerably improved as compared to the previously described absorbers based on renewable raw materials.

The polymer composition according to the present invention may particularly be used as absorbent as a fiber, film, powder, or granular material to absorb water or aqueous liquids, such as urine and blood, and therefore is particularly suitable for the use in diapers, tampons, surgical products, cable sheathings, culture pots, packaging materials for meat or fish, and in absorbent garments.

Additionally, the material is suitable as storage medium for the gradual release of active substances, such as drugs, pesticides (U.S. Pat. No. 4,818,534; U.S. Pat. No. 4,983,389; U.S. Pat. No. 4,983,390; U.S. Pat. No. 4,985,251) and fragrances, having the advantage that the storage medium is degradable.

Therefore, an additional advantage results in the fact that the active substance is released completely.

The active substance-containing depot materials may be manufactured by absorption, preferably of concentrated, aqueous or hydrous solutions, into the substantially dry absorber, and renewed drying, if necessary.

The active substance may also be added directly or as a solution or dispersion in any previous stage of the production process of the absorber composition.

The active substance-containing depot materials are used in the form of a powder or as a dispersion in hydrophobic media, which may comprise dispersion stabilizers, such as emulsifiers or stabilizers, or in admixture with other substances, such as polysaccharides.

For instance, the addition of these bactericide-containing depot materials to cellulose, guar or starch products or their derivatives, such as carboxymethylcellulose, prevents the decomposition of these substances during storage and application in aqueous media over a longer period of time, thus avoiding larger amounts of free active substance in the solution owing to the depot effect.

Test methods:
Tea Bag Test (TBT)

To determine the absorption capacity a tea bag test was carried out. An aqueous 0.9% NaCl-solution was used as test solution.

0.2 g of a test substance (screened to between 90 and 630 μm), which had been weighed into a tea bag, was allowed to swell in the test solution for 10 and 30 minutes, respectively. After dripping for 5 minutes (maximum value), centrifuging was effected in a centrifuge, e.g., in a commercial spin dryer, at 1400 rpm. The liquid absorption was determined gravimetrically and expressed in terms of 1 g of substance (retention value).

Absorption under Load (AUL)

To determine the liquid absorption capacity under a load, the absorption under load—as described in EP-A-0 339 461—was determined.

0.16 g test substance (screened to between 300 and 600 µm) was allowed to swell by capillary action in 0.9% NaCl-solution for 60 minutes under a pressure of 1.55 kN/m$^2$ (99.8 g/in$^2$). The liquid absorption was determined gravimetrically and expressed in terms of 1 g of substance.

Gel strength (G')

To determine the gel strength G' of the swollen absorbers the method described in EP-A-0 339 461 was used.

Apparatus: Controlled Stress Rheometer CS 100, (Carri-Med Ltd. Dorking/UK).

Measurement conditions: Plate-plate-system, diameter 60 mm, space between the plates 2 mm, temperature 20° C., torque 1000–4000 µNm, amplitude 1.5–5 mrad, frequency 10.0 Hz, 28 ml 0.9% NaCl/g absorber. The indications are given in N/m$^2$.

Flow Test (FT)

By means of the flow test the velocity at which the products absorbed the test liquid was determined; moreover, it was examined whether they showed blocking phenomena, whether they were completely swollen and whether they were wetted all over. Furthermore, it was examined whether the gels were present in a solid, tacky or loose and separated form.

To carry out the flow test, about 100 mg of substance were placed on a water-soaked paper cloth, and the water absorption by the products was observed. The absorption behavior was evaluated according to the following graduation:

A: is absorbed rapidly
B: is absorbed very rapidly
C: is absorbed from beginning to end
D: after water absorption gel is present in separated form
E: gel blocking.

EXAMPLE 1

8 g C.M.C. Walocel 40 000 (sodium carboxymethylcellulose, product of Wolff Walsrode) is thoroughly mixed with 2 g Favor® SAB 953 (cross-linked, partially neutralized sodium polyacrylate; product of Stockhausen GmbH), 0.5 g TONE 230 (polyol based on caprolactane, molecular weight 1250 g/mole, product of Union Carbide), 0.1 g titanyl sulfate, and 0.5 g Al(OH)$_2$OOCCH$_3$*⅓ H$_3$BO$_3$ by using 2 ml isopropanol and 1 ml water, and heated in the oven to 120° C. for 60 minutes.

TBT (max./ret.)=51 g/g / 33 g/g; AUL=15.4 g/g; FT: B C D

EXAMPLE 2

Procedure as in Example 1, however, the added quantity of titanyl sulfate is increased to 0.25 g.

TBT (max./ret.)=47 g/g / 29 g/g; AUL=17.5 g/g; FT: B C D

EXAMPLE 3

Procedure as in Example 1, however, the added quantity of titanyl sulfate is increased to 0.5 g.

TBT (max./ret.)=46 g/g / 28 g/g; AUL=17.7 g/g; FT: B C D

EXAMPLE 4

Procedure as in Example 2, however, 0.5 g fiber BE 600/30 (cellulose, diameter 17 mm, length 30 mm, product of Rettenmaier) is additionally incorporated.

TBT (max./ret.)=48 g/g / 32 g/g; AUL=17.4 g/g; FT: A C D

EXAMPLE 5

60 g C.M.C., Walocal 40000 is thoroughly mixed with 1.5 g ethylene carbonate, 1.5 ml isopropanol, and 1.5 ml water followed by oven-heating to 120° C. for one hour. 8 g of this product is thoroughly mixed with 2 g Favor SAB 953, 0.5 g TONE 230, 0.5 g fiber BE 600/30, 0.25 g titanyl sulfate, 1 ml water, and 2 ml i-propanol and then heated to 120° C. for one hour in the oven.

TBT (max./ret.)=46 g/g / 28 g/g; AUL=18.2 g/g; FT: B C D

EXAMPLE 6

Procedure as in Example 5, however, instead of 0.5 g fiber, 1.0 g of this fiber is used.

TBT (max./ret.)=43 g/g / 26 g/g; AUL=17.5 g/g; FT: B C

EXAMPLE 7

Procedure as in Example 3, however, 0.5 g fiber BE 600/30 is additionally used. Furthermore, 1.0 g triglycerol monostearate is used instead of TONE 230.

TBT (max./ret.)=35 g/g / 24 g/g; AUL=17.8 g/g; FT: C D

EXAMPLE 8

Procedure as in Example 4, however, 1.0 g of fiber BE 600/30 is added, additionally the mixture is heated in the oven to 120° C. for 1.5 hours instead of one hour.

TBT (max./ret.)=47 g/g / 31 g/g; AUL=19.0 g/g; FT: A C D

EXAMPLE 9

100 g of the product obtained in Example 1 is mixed with 100 ml of a 0.125% aqueous solution of 3,7-bis (dimethylamino)-phenothiazinium chloride and then dried at 60° C. in the recirculating air dryer for 2 h.

200 mg of the product thus obtained are placed in a tea bag. This is suspended in a beaker with 50 ml 0.2% solution of sodium chloride. After one hour, the tea bag is removed. The dye of the sodium chloride solution is assessed, then the procedure is repeated with fresh NaCl-solution. Even after the 5th cycle, the blueness of the sodium chloride solution shows the release of the active substance from the polymer composition serving as storage medium.

COMPARATIVE EXAMPLE 1

Procedure as in Example 3, however, 0.5 g titanium dioxide is used instead of the titanyl sulfate.

TBT (max./ret.)=47 g/g / 32 g/g; AUL=10.6 g/g; FT: E

COMPARATIVE EXAMPLES 2, 3

Examples 3 and 5 are repeated without the addition of TONE 230. The products are inhomogeneous and separate readily. For this reason, no reproducible analytical data can be obtained.

COMPARATIVE EXAMPLE 4

Procedure as in Example 4, however, no titanyl sulfate is added.

TBT (max./ret.)=45 g/g / 33 g/g; AUL=9.9 g/g; FT: A C D

We claim:

1. An absorbent polymer composition comprising:
    (A) 70–99.99%-wt. of component A, wherein said component A is a water-soluble or water-swellable polysaccharide or polysaccharide derivative selected from the group consisting of carboxymethyl guar, hydroxyethylcellulose, hydroxypropylcellulose, carboxymethylcellulose and carboxymethyl starch, which polysaccharide or polysaccharide derivative may optionally be modified by cross-linkage, and (B) 0.01–30%-wt. of component B, wherein said component B is a water-swellable, synthetic polymer or copolymer of polymeric subunits selected from the group consisting of (meth-)acrylic acid, (meth-)acrylonitrile, (meth-)acrylamide, vinyl acetate, vinyl pyrrolidone, vinyl pyridine, maleic acid or anhydride, itaconic acid or anhydride, fumaric acid, vinyl sulfonic acid, 2-acrylamido-2-methylpropane sulfonic acid, and the amides, the N-alkyl derivatives, the N,N'-dialkyl derivatives, the hydroxyl group-containing esters, and the amino group-containing esters of said subunits, wherein 0–98%-wt. of any acid groups may be neutralized, and wherein said polymer or copolymer is cross-linked by an at least bifunctional compound, wherein the recited weight percentages of said components A and B are based on the total weight of components A and B, and (C) 0.1–30%-wt., relative to said polymer components A and B, of an organic matrix material having a melting or softening point, respectively, of below 180° C., wherein said organic matrix material prevents separation and gel blocking of said absorbent polymer composition, and (D) 0.001 to 10%-wt., relative to said two polymer components A and B, of an ionic or covalent cross-linking agent, wherein said cross-linking agent cross-links said components A and B with each other, and (E) 0.1 to 50%-wt., relative to said polymer components A and B, of at least one reactive additive, wherein said reactive additive improves the absorption capacity and the absorption rate of said absorbent polymer composition, and (F) 0–50%-wt., relative to said polymer components A and B, of at least one anti-blocking agent.

2. An active substance-containing composition comprising the absorbent polymer composition according to claim 1 and at least one active substance.

3. The composition according to claim 1, wherein said composition comprises 75–95%-wt. of said component A, 10–25%-wt. of said component B, 2.5–7.5%-wt., relative to said components A and B, of at least one said organic matrix material (C), 3–7%-wt., relative to said components A and B, of at least one said ionic or covalent cross-linking agent (D), 2–10%-wt., relative to said polymer components A and B, of at least one said reactive additive (E), and 0.5–50%-wt., relative to said components A and B, of at least one said anti-blocking agent (F).

4. The composition according to claim 1 wherein said polysaccharide or polysaccharide derivative is selected from the group consisting of starch, guar, cellulose, carboxymethyl guar, hydroxyethylcellulose, hydroxypropylcellulose, carboxymethylcellulose and carboxymethyl starch.

5. The composition according to claim 3 wherein said organic matrix material is selected from the group consisting of triglycerol monostearate, castor oil, wax esters, and polycaprolactones, which are optionally modified by reaction with maleic anhydride.

6. The composition according to claim 1 wherein said ionic cross-linking agent is selected from metallic compounds in the form of their salts with organic and inorganic acids.

7. The composition according to claim 1, wherein said covalent cross-linking agent (D) is a compound selected from the group consisting of polyfunctional carboxylic acids, alcohols, amines, epoxides, carboxylic acid anhydrides, aldehydes, and heterofunctional compounds comprising at least two functional groups of compounds selected from the group consisting of polyfunctional carboxylic acids, alcohols, amines, epoxy compounds, carboxylic acid anhydrides, and aldehydes.

8. The composition according to claim 1 wherein said reactive additive is selected from the group consisting of natural and synthetic surfactants, ion-exchangers, hydrolyzable metallic salts and metal salt complexes.

9. The composition according to claim 8, wherein said reactive additive is titanyl sulfate.

10. A process for the production of an absorbent polymer composition according to claim 1, comprising the steps of:
(A) mixing said components A–F to homogeneity, and
(B) heat-treating the resulting mixture of components A–F to effect fixing of said cross-linking agent by said organic matrix compound.

11. The process according to claim 10 wherein said components A and B are screened to a particle size of 90 μm–630 μm, prior to mixing.

12. The process according to claim 10 wherein said step (A) of mixing said components A–F to homogeneity comprises:

mixing said components A and B, then, mixing thereto to homogeneity said anti-blocking agent E, said reactive additive E, and said organic matrix material C, subjecting the resulting mixture of components A, B C, E and F to a first heat treatment at 25° C. to 180° C., and adding said cross-linking agent D, and wherein said step (B) of heat-treating the resulting mixture of components A–F comprises subjecting said mixture to a second heat-treatment at 25° C. to 180° C.

13. The process according to claim 10, wherein a hydrophilic solvent is added to said mixture of components A–F, prior to said step (B) of heat-treating said mixture of components A–F.

14. The process according to claim 13 wherein said solvent is water or a mixture of water with a hydrophilic organic solvent.

15. The absorbent polymer composition according to claim 1, wherein said composition is contained in a fiber, film, powder, or granular material.

16. A composition comprising the absorbent composition of claim 1, wherein said absorbent composition is in the form of a powder or is dispersed in hydrophobic media.

17. The active substance-containing composition according to claim 2, wherein said active substance is selected from the group consisting of drugs, pesticides, bactericides and perfumes.

18. The active substance-containing composition according to claim 2, wherein said composition releases said active substance in a retarded manner.

19. The composition according to claim 3, where said composition comprises 5–15%-wt., relative to said components A and B, of at least one said anti-blocking agent.

20. The composition according to claim 4, wherein said component A is carboxymethylcellulose.

21. The composition according to claim 6, wherein said metallic compounds are selected from the group consisting of water-soluble magnesium, calcium, aluminum, zirconium, iron and zinc compounds.

22. The composition according to claim 8, wherein said ion exchangers are cation exchangers.

23. The process according to claim 12, wherein said first heat-treatment is carried out at from 100° C. to 120° C.

24. The process according to claim 12, wherein said second heat-treatment is carried out at from 50° C. to 80° C.

25. The process according to claim 10, wherein said step (B) of heat-treating said mixture of components A–F is carried out at 25° C. to 180° C.

26. The process according to claim 25, wherein said step (B) of heat-treating said mixture of components A–F is carried out at 100° C. to 120° C.

27. The process according to claim 13, wherein said hydrophilic solvent is added in an amount of 1–10%-wt., based on the weight of said mixture of components A–F.

28. The process according to claim 14, wherein said solvent is a mixture of water and isopropanol.

29. The process according to claim 10, further comprising the step of contacting said absorbent polymer composition with an aqueous or hydrous solution comprising an active substance, whereby said active substance is absorbed by said absorbent polymer composition, thereby forming a depot material composition.

30. The process according to claim 10, further comprising the step of adding an active agent to the mixture at any of the steps, thereby forming a depot material composition.

31. An article comprising the absorbent polymer composition of claim 15, wherein said article is selected from the group consisting of packaging materials, culture pots, cable sheathing, tampons, diapers and animal hygiene products.

32. A composition according to claim 16, wherein said composition further comprises a dispersion stabilizer.

33. The composition according to claim 1, wherein the covalent cross-linking agent (D) is a compound selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate, and heterofunctional compounds comprising at least two functional groups of compounds selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate.

34. The process according to claim 10, wherein the covalent cross-linking agent (D) is a compound selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate, and heterofunctional compounds comprising at least two functional groups of compounds selected from the group consisting of citric acid, mucic acid, tartaric acid, malic acid, malonic acid, succinic acid, glutaric acid, adipic acid, polyethylene glycols, glycerol, propanediols, polyoxypropylene amines, epichlorohydrin, ethylene glycol diglycidyl ether, glycol diglycidyl ether, succinic anhydride, maleic anhydride, ethylene carbonate and propylene carbonate.

* * * * *